(12) United States Patent
Suárez et al.

(10) Patent No.: US 9,846,154 B2
(45) Date of Patent: Dec. 19, 2017

(54) OPTICAL METHOD AND DEVICE FOR IDENTIFYING AND QUANTIFYING ANALYTES

(71) Applicant: ECOLE POLYTECHNIQUE FEDERALE DE LAUSANNE (EPFL), Lausanne (CH)

(72) Inventors: Guillaume Suárez, Lussery-Villars (CH); Christian Santschi, Lausanne (CH); Olivier Martin, Pully (CH)

(73) Assignee: Ecole Polytechnique Fédérale de Lausanne (EPFL), Lausanne (CH)

( * ) Notice: Subject to any disclaimer, the term of this patent is extended or adjusted under 35 U.S.C. 154(b) by 12 days.

(21) Appl. No.: 14/366,597

(22) PCT Filed: Dec. 20, 2012

(86) PCT No.: PCT/IB2012/057504
§ 371 (c)(1),
(2) Date: Jun. 18, 2014

(87) PCT Pub. No.: WO2013/093817
PCT Pub. Date: Jun. 27, 2013

(65) Prior Publication Data
US 2014/0322733 A1  Oct. 30, 2014

(30) Foreign Application Priority Data
Dec. 20, 2011 (WO) .................. PCT/IB2011/055819

(51) Int. Cl.
*G01N 21/75* (2006.01)
*G01N 33/573* (2006.01)
(Continued)

(52) U.S. Cl.
CPC ............. *G01N 33/573* (2013.01); *C12Q 1/26* (2013.01); *G01N 21/314* (2013.01)

(58) Field of Classification Search
CPC .... G01N 33/573; G01N 33/585; G01N 21/47; G01N 21/314; G01N 33/54313; C12Q 1/26
See application file for complete search history.

(56) References Cited

U.S. PATENT DOCUMENTS 5,879,294 A  3/1999 Anderson et al.
6,473,632 B1  10/2002 Myers
(Continued)

FOREIGN PATENT DOCUMENTS

EP   0 816 829 A2   1/1998
EP   0816829 A2    7/1998
(Continued)

OTHER PUBLICATIONS

Liu, G.L. and Lee, L.P., Optical Sensing of Electrochemical Reactions on a Bio-Hybrid Nanoparticle, 2005, Proceedings of SPIE, vol. 5705, pp. 123-130.*
(Continued)

*Primary Examiner* — Erik B Crawford
(74) *Attorney, Agent, or Firm* — Nixon & Vanderhye P.C.

(57) ABSTRACT

A method for analyzing a metalloprotein and/or the interaction with its environment comprising the following steps: (a) Providing a medium that enhances the detection of the electromagnetic cross-section signal of metalloproteins, (b) Incorporating a metalloprotein to analyse into said medium, (c) Contacting said medium with electromagnetic radiation, (d) Obtaining the electromagnetic cross-section spectrum of said metalloprotein, (e) Determining from said electromagnetic cross-section spectrum at least one parameter related to one or several analytes of interest.

11 Claims, 3 Drawing Sheets

(51) Int. Cl.
*G01N 21/31* (2006.01)
*C12Q 1/26* (2006.01)

(56) References Cited

U.S. PATENT DOCUMENTS

| 2004/0023291 | A1 | 2/2004 | Spertini | |
|---|---|---|---|---|
| 2006/0145170 | A1* | 7/2006 | Cho | H01L 33/22 |
| | | | | 257/95 |
| 2009/0053736 | A1 | 2/2009 | Mattingly et al. | |
| 2010/0196920 | A1 | 8/2010 | Lee et al. | |
| 2010/0231899 | A1* | 9/2010 | Hulko | C12Q 1/005 |
| | | | | 356/218 |

FOREIGN PATENT DOCUMENTS

| EP | 1 640 710 A1 | 3/2006 |
|---|---|---|
| EP | 1640710 A1 | 3/2006 |
| WO | 2006/108183 A2 | 10/2006 |
| WO | WO2006108183 A2 | 10/2006 |
| WO | 2008/010843 A2 | 1/2008 |
| WO | WO2008010843 A2 | 1/2008 |
| WO | 2008/140754 A1 | 11/2008 |
| WO | WO2008140754 A1 | 11/2008 |

OTHER PUBLICATIONS

Suarez et al., "Biophotonic tool for sensing the dynamics of HOextracellular release in stressed cells", *Optical Diagnostics and Sensing XII: Toward Point-of-Care Diagnostics; and Design and Performance Validation of Phantoms Used in Conjunction with Optical Measurements of Tissue IV*, SPIE, 1000 20$^{th}$ St. Bellingham, WA, vol. 8229, No. 1, Feb. 9, 2012, pp. 1-7.

Dutta-Gupta et al., :Ultrasensitive system for the real-time detection of HObased on strong coupling in a bioplasmic system, *Plasmonics in Biology and Medicine IX*, SPIE, 1000 20$^{th}$ St. Bellingham, WA, vol. 8234, No. 1, Feb. 9, 2012, pp. 1-6.

International Search Report for PCT/IB2012/057504, dated Jun. 24, 2013.

Written Opinion of the ISA for PCT/IB2012/057504, dated Jun. 24, 2013.

Kykyneshi, Robert, et al., Chapter 6: Transparent Conducting Oxides Based on Tin Oxide, Handbook of Transparent Conductors, 2010, pp. 171-172.

Wang, Yude, et al., "Ordered Mesoporous Sb-, Nb-, and Ta-Doped SnO2 Thin Films with Adjustable Doping Levels and High Electrical Conductivity," ACSNANO, vol. 3, No. 6, 2009, pp. 1373-1378.

* cited by examiner

OPTICAL METHOD AND DEVICE FOR IDENTIFYING AND QUANTIFYING ANALYTES

This application is the U.S. national phase of International Application No. PCT/IB2012/057504 filed 20 Dec. 2012 which designated the U.S. and claims priority to International Application No. PCT/IB2011/055819 filed 20 Dec. 2011, the entire contents of each of which are hereby incorporated by reference.

FIELD OF INVENTION

The present invention relates to optical methods and devices for identifying and quantifying analytes. It more precisely relates to the analysis of metalloproteins and/or the interaction with their environment.

BACKGROUND

One approach commonly used for identifying a change that occurs in a cell consists in detecting a target analyte. See for instance international patent application WO 2008140754.

The measurement of analytes that are important players in chemical, biological, physiological, environmental and other systems can lead to more insights into complex mechanisms. Additionally, the real-time detection of those analytes can provide information on their concentration, fate, or even on their physiological function or effect on cells and organisms. A large variety of detection approaches have been developed that are based on spectroscopic methods. In that context, the use of signal-enhancing structures for Raman spectroscopy has raised a large interest, as illustrated by the fractal structures employed by Ginzburg et al. for the detection of antioxidants [see for instance US patent application U.S. 2004023291]. Others focused on the improvement of methods for non-invasive and in-vivo detection of physiological parameters. For instance, Anderson et al. proposed to use the second derivative spectral values of absorption at two wavelengths of irradiation in order to measure the relative concentration of chromophores, such as haemoglobin, in tissue samples [See e.g. European patent applications EP 1 640 710 and EP 0 816 829]. Differently, the need for integrated detection methods with high throughput has led to the development of platforms that combine standard end-point biomolecule assays and "omic" technologies. Such approach has been suggested as a toxicological platform to evaluate the potential toxic effects of nanomaterials on cells [see international patent application WO 2008010843]. On their side, Fang et al. developed a label-free biosensor that relies on the measurement of the directional mass redistribution in adherent layers of cells exposed to a variety of stimuli [International patent application WO 2006108183].

Hydrogen peroxide ($H_2O_2$) belongs to the reactive oxygen species (ROS) of great importance in fields such as biology, pharmaceutics, environment, clinical analysis or food manufacturing. Especially in living organisms $H_2O_2$ plays an important role as signalling molecule to regulate biological processes but it is also known for its cytotoxic effects. ROS are principally generated by metabolic processes in the mitochondrial electron transport chain and, especially $H_2O_2$, is produced as a side product by many enzymatic reactions. Increased production of $H_2O_2$ is associated with oxidative stress which is thought to be involved in the development of many incurable deceases including cancer, Parkinson's decease and Schizophrenia, to name a few examples. End-point bioassays based on membrane-permeable fluorescent and chemiluminescent probes are currently the most widely used to evidence oxidative stress and ROS, including $H_2O_2$, production in biological cells exposed to different sources of stress. Those optical methods are very sensitive with detections limits in the pM range. However, fluorescent dyes photo bleaching is one of the major drawback of these optical methods. Furthermore, those indirect techniques are invasive due to the requirement of additional chemicals leading to interferences with the system under observation, which is particularly problematic for measurements in biological systems. Recently, fluorescent single-wall carbon nanotube arrays were used to detect at the μM range $H_2O_2$ involved in signalling of epidermal growth factor receptors on the membrane of human carcinoma cells. In addition, the spin-trapping electron spin resonance technique enables real-time probing of intra- and extra-cellular free radical ROS via the formation of semi-stable paramagnetic compounds. On the other hand, electrochemical biosensors, with published detection limits on the order of tens of nanomolars, represent a promising alternative offering non-invasive tracking of the ROS released from cell compartments. Those methods allow real-time measurements but the process performance is limited by slow electrode kinetics and large interferences which may occur due to the availability of other electroactive species in real samples.

DESCRIPTION OF THE INVENTION

The present invention provides a new method and a new device for analysing metalloproteins and/or the interaction with their environment.

1) To this effect the invention consists in a method for analysing a metalloprotein and/or the interaction with its environment which comprises the following steps:

a) Providing a medium that enhances the detection of the electromagnetic cross-section of metalloproteins, (b) Incorporating a metalloprotein to analyse into said medium, (c) Contacting said medium with an electromagnetic radiation, (d) Obtaining the electromagnetic cross-section spectrum of said metalloprotein, (e) Determining from said cross-section spectrum at least one parameter related to one or several analytes of interest.

2) Different types of media that enhance the detection of the electromagnetic cross-section of metalloproteins can be used, for instance: (a) multiscattering aggregates and metalloproteins, (b) multiscattering suspensions and metalloproteins, (c) porous materials and metalloproteins, (d) porous membranes and metalloproteins (e) gels and metalloproteins, (f) structured substrates and metalloproteins, (g) resonant and non-resonant non-plasmonic structures and metalloproteins, (h) resonant and non-resonant plasmonic structures.

3) In one embodiment, the scattering substrates from 2)(a)-(g) generate a multiscattering of the incident light leading to an amplification of the electromagnetic cross-section signal of the metalloprotein. In yet another embodiment, the plasmonic structures from 2) (h) enhance the detection of the electromagnetic cross-section of metalloproteins.

4) The molecular state coefficient of the metalloproteins which is determined through the analysis of its electromagnetic cross-section spectrum can be linked to the concentration of the analyte by a calibration curve.

5) The invention provides a method for measuring the concentration of a variety of analytes that modify the electromagnetic cross-section spectrum of metalloproteins, either directly via binding or catalysis, or indirectly through their transformation into reacting analytes.

The invention will be better understood below with a more detailed description illustrated by non-limiting examples.

Figure 1:
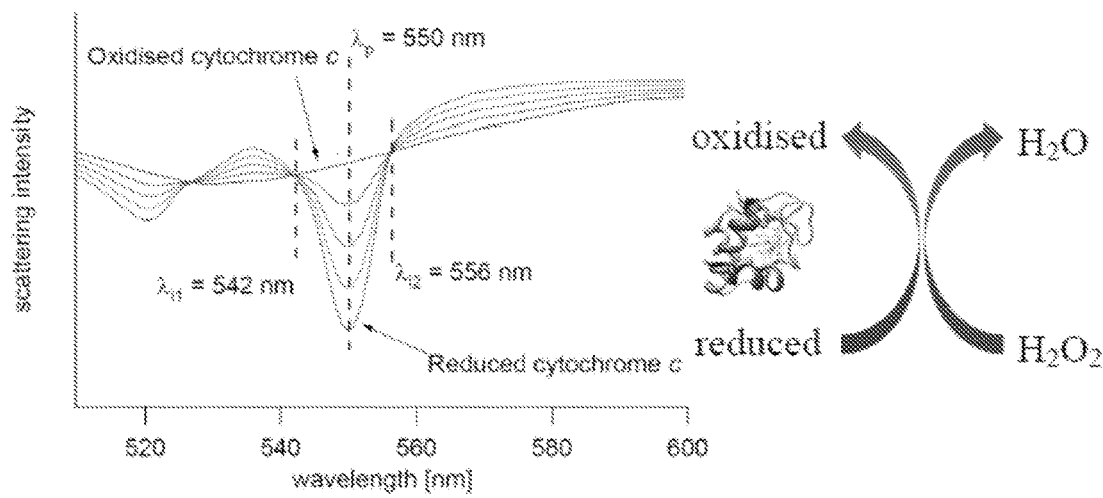
FIG. 1: Optical spectra of reduced and oxidised cytochrome c (cyt c) showing a well pronounced absorption peak at 550 nm and a weak peak at 530 nm, respectively. The degree of strength of the absorption peak provides an indicator allowing quantification of the average redox state of cyt c.
Figure 2:
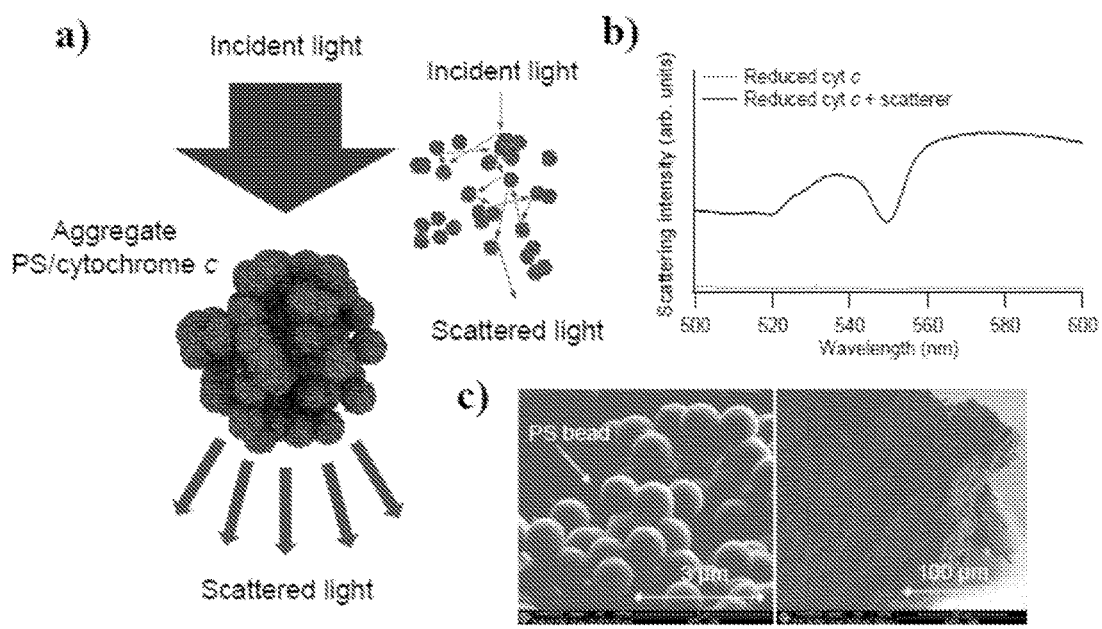
FIG. 2: a) Schematic illustration displaying the multiscattering amplification. b) Absorption signal enhancement as proven by comparing spectra of cyt c recorded in bright- and dark-field configurations. c) FIB-image of polystyrene/cyt c aggregate. The clump of polystyrene beads is held together by cross-linked cyt c.
Figure 3:
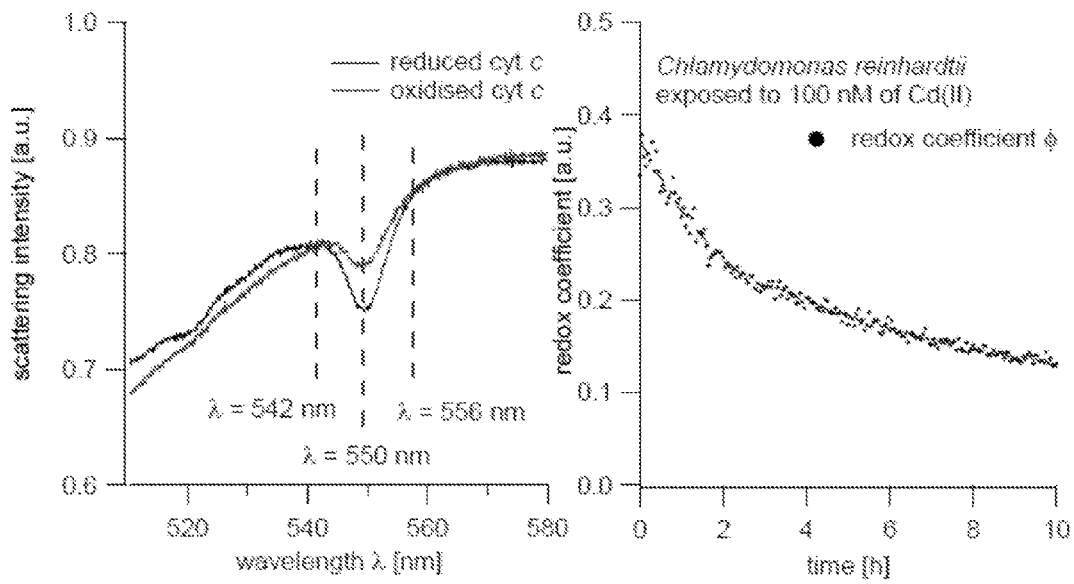
FIG. 3: a) Spectra of partially reduced and oxidised cyt c. In that example, the cyt c is reduced by extracellular $H_2O_2$ released by phytoplanktonic cells, *Chlamydomonas reinhardtii*, exposed to Cd(II). b) Time-evolution of the calculated redox coefficient allowing real-time detection of extracellular $H_2O_2$ released by *C. reinhardtii*.

As mentioned above ROS play a key role in cell signalling and oxidative stress mechanisms, therefore sensing its production by living organisms is of fundamental interest. The method is based on the measurement of the optical absorption spectra of the hemoprotein cytochrome c with respect to the oxidation state of its ferrous $Fe^{II}$ and ferric $Fe^{III}$ heme group. In contrast to existing techniques, this approach enables non-invasive continuous real-time measurements with high sensitivity in the sub-nM range. Dynamic information on the modification of the cell oxidative status of *C. reinhardtii* was obtained under oxidative stress conditions, where the increase of $H_2O_2$ production rates in the presence of trace concentrations of Cd(II) was evidenced. Furthermore, the dynamics of $H_2O_2$ production was investigated under different lighting conditions and different production rates were observed. This evidences the impact of Cd(II) on the photosynthetic activity of those phytoplanktonic cells. The critical role that $H_2O_2$ and other reactive oxygen species (ROS) play in cell physiology is complex and multifaceted. ROS (over)production is involved in cell signalling and in oxidative stress mechanisms that can lead to lipidic/nucleic peroxidation and cell death. Therefore, in parallel to the systems biology perspective supported by genomics, proteomics, and metabolomics, the development of an analytical tools providing information on the dynamics of ROS generation remains essential to gain further insights into the complex physiological processes of living cells and their response to environmental stress.

EXAMPLE 1

The biosensor presented in this example relies on the ultra-sensitive optical detection of the redox state of cytochrome c (cyt c). Cyt c exhibits different absorption peaks in its oxidised, respectively reduced states: a broad peak at $\lambda=530$ nm, respectively narrower peaks at $\lambda=520$ and $\lambda=550$ nm. The redox catalytic activity of cyt c, the so-called pseudo-peroxidase behaviour, in which the ferrous $Fe^{II}$ heme group is oxidised into the ferric $Fe^{III}$ heme group leading to $H_2O_2$ reduction into water, provides the spectroscopic information exploited here. The temporal evolution of cyt c spectra is followed using an inverted microscope in dark field configuration. Using aggregates of cyt c/polystyrene beads (500 nm diameter) with large scattering cross-sections $\sigma_s$, the background is efficiently suppressed leading to an enhanced signal-to-background ratio (note that in the bright field configuration no measurable signal is detected). The raw cyt c spectra are converted to the normalized oxidation state coefficient $\phi$. $\phi$ corresponds to the average oxidation state of the cyt c present in the aggregate. It ranges between 0 and 1 for fully oxidized and reduced samples, respectively. $\phi$ variation for increasing $H_2O_2$ concentration exhibits the typical sigmoidal shape of ligand binding assays, which can be fitted with the 4-parameter logistic model. Starting the experiment with a partially reduced cyt c sample stabilized in HEPES buffer solution, the value of $\phi$ decreases with $H_2O_2$ concentration over a dynamic range from 10 pM to 1 μM. The calculated limit of detection is below 100 pM of $H_2O_2$. This low limit of detection and extended dynamic range make the biosensor a promising tool for real-time measurements of traces of $H_2O_2$ in the surrounding living cells. The dynamics of $H_2O_2$ release by green microalgae *C. reinhardtii* exposed to nanomolar trace concentrations of Cd(II) has been explored. *C. reinhardtii* is a photosynthetic microalga and a major primary producer at the origin of the food chain in aquatic systems. In addition to its environmental relevance, the completion of the *C. reinhardtii* genome project, revealed this microorganism as a useful model to investigate molecular cellular processes. Cadmium is a widespread environmental toxicant known to cause adverse effects in algae, including growth and chlorophyll synthesis inhibition increase in the superoxide dismutase activity, phytochelatine induction, and oxidative stress. *C. reinhardtii* homeostasis and tolerance to Cd(II) are well documented and the following chronological lethal sequence has been reported: oxidative stress, lipid and nucleic acid peroxidation, cell structure alteration, mutagenesis and apoptosis. However, most of the ecotoxicological studies analysing the effects of Cd(II) contamination rely on acute stress conditions with Cd(II) concentrations in the range of hundreds of micromolar that strongly contrast with environmental concentrations in fresh water lying in the sub-micromolar range. Recent studies have examined the intracellular ROS generation by flow cytometry and the global expression profile of *C. reinhardtii* under short term exposure conditions (typically a few hours) to environmentally relevant concentrations of Cd(II).

With this in mind we have measured in real-time the concentrations of $H_2O_2$ in a suspension of *C. reinhardtii* ($2 \times 10^{-6}$ cell $mL^{-1}$) exposed to 10 and 50 nM of Cd(II) as well as unexposed controls in order to obtain dynamic information on cell oxidative status changes over a period of 300 min. In the absence of Cd(II) the $H_2O_2$ production inherent to the physiological activity of *C. reinhardtii* reached $3\times10^{-4}$ molecule cell$^{-1}$. The variation $\Delta\phi$ of the oxidation state coefficient over time revealed an overproduction of $H_2O_2$ in *C. reinhardtii* exposed to 10 and 50 nM of Cd(II) with respect to the non-exposed cells. The total amount of $H_2O_2$ production over the 300 min period, obtained from the conversion of $\Delta\phi$ values into concentration, is $10^5$, respectively $10^8$, molecules of $H_2O_2$ per algal cell exposed to 10,respectively 50 nM of Cd(II). The $H_2O_2$ production increase per algal cell with Cd(II) concentration in the exposure medium is consistent with the Cd(II) increase observed intracellularly. Similar incidence of sublethal Cd(II) concentrations on either the intracellular ROS production or gene expression levels has already been observed after 2.5 and 2 hours exposition time, respectively. These findings not only agree with the general believe that the Cd(II) toxicity mechanisms are associated with the generation of ROS, but also demonstrate the capabilities of this approach to obtain quantitative information and, thus, further insights into the dynamics of Cd(II) toxicity mechanisms. Furthermore, real-time detection gives access to the production rate of $H_2O_2$ in algae exposed to Cd(II) and can further our understanding of the corresponding kinetics. The control experiment in the absence of Cd(II) revealed that the $H_2O_2$ production rate by *C. reinhardtii* increased progressively from 20 to 150 molecule min$^{-1}$ cell$^{-1}$ after a lag period on the order of 40 min. Using the typical chlorophyll content in *C. reinhardtii* ($2.2\times10^{-6}$ (mg Chl)$^{-1}$ h$^{-1}$) we can estimate the $H_2O_2$ production rate on the order of a few units of pmol $H_2O_2$ (mg Chl$^{-1}$ h$^{-1}$. Addition of 10 and 50 nM Cd(II) to algal suspensions results in more complex $H_2O_2$ production rate profiles. The initial plateau in the interval from t=20 to 40 min corresponding to $7\times10^2$ and $7\times10^4$ molecule min$^{-1}$ cell$^{-1}$ for 10 and 50 nM Cd(II), respectively, is followed by a gradual decrease of the production rates. A minimum is observed at 110 and 160 min for algae exposed to 10 and 50 nM of Cd(II), respectively. A longer exposure time results in a sharp increase of the production rates reaching $2.6\times10^3$ and $7\times10^5$ molecule min$^{-1}$ cell$^{-1}$ after 300 min. The observed evolution of the $H_2O_2$ production rate suggests that, after an adaptive period which depends on the Cd(II) concentration, antioxidant levels can balance efficiently the accumulation of the ROS within the cell. Indeed up-regulation of intracellular antioxidant glutathione levels in *C. reinhardtii* after exposure to 80 nM of Cd(II) was observed for a similar exposure time. Our data agree also with proteomic studies showing up-regulation of antioxidant proteins such as L-ascorbate peroxidase or superoxide dismutase in *C. reinhardtii*. However, this period is then followed by a further increase of the $H_2O_2$ production rate, suggesting that over a prolonged exposure the antioxidant system is incapable to balance the excessive ROS production in the cell.

EXAMPLE 2

We examined the possibility to study the dynamics of $H_2O_2$ release under Cd(II) exposure in the context of photosynthesis. It is known that ROS released from photosynthetic organisms generally originate from the photosystems II and I (PSII and PSI) located in the thylakoid membrane of the chloroplast where $O_2$ is reduced to $O_2^-$. This transformation is at the beginning of a reaction cascade that leads to the formation of $H_2O_2$ and hydroxyl radicals. The light driven water splitting reaction in PSII provides dioxygen $O_2$ whose one-electron reduction is needed to initiate a reaction cascade leading to $H_2O_2$. Previous studies carried out on *C. reinhardtii* have shown that the chloroplasts are readily accessible to Cd(II) and the latter causes disorders on both the electron donor and acceptor sides of PSII, leading to the disruption of the photosynthetic chain. Moreover, it has been recently demonstrated that despite the stromatic antioxidant system, choloroplast-derived $H_2O_2$ is able to diffuse, most likely through aquaporins, out of chloroplasts. In the experiment *C. reinhardtii* was exposed to 100 nM of Cd(II) at t=0 and maintained under either light or quasi-dark conditions (in the latter, light is on only 7 s per min in order to record the cyt c absorption spectrum) while monitoring the oxidative state coefficient $\Delta\phi$. The lack of illumination induces a delay of about 3 h in the overproduction of $H_2O_2$ in response to Cd(II) exposure. The analysis of the $H_2O_2$ production rates stresses a similar time-lag between light and quasi-dark situations, with a rate of $10^8$ molecule min$^{-1}$ cell$^{-1}$ reached at t=120 and t=320 min, respectively. The succession of quasi-dark and light periods during the experiment provides further evidence of the impact of Cd(II) on the photosynthetic apparatus. The time constants, calculated for the corresponding periods illustrate clearly that the overproduced $H_2O_2$ is correlated with the light driven electron extraction from water-splitting complex which is known to remain functional at submicromolar Cd(II) concentrations. It is likely that the overproduction of light-dependent $H_2O_2$ originates at the PSII acceptor side, as a consequence of disturbed electron transport from PSII towards PSI by Cd(II) binding to the plastoquinone pool.

EXAMPLE 3

Figure 4:
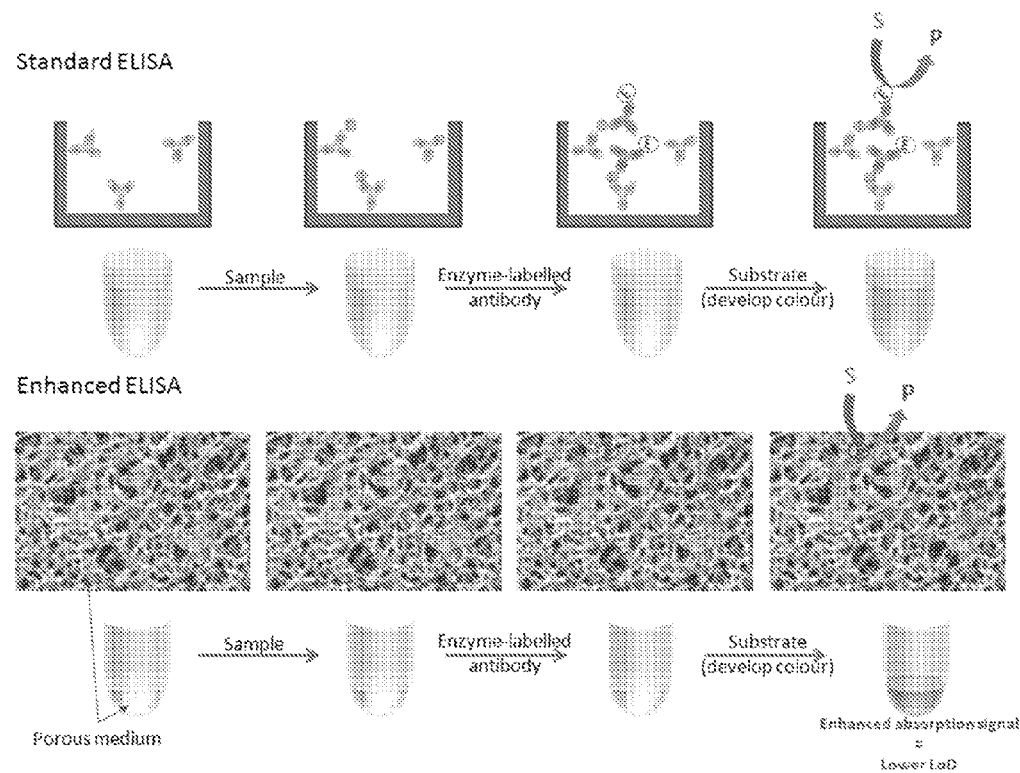
FIG. 4: Schematic representation of step-to-step operational sequence for standard and enhanced ELISA. The presence of a scattering porous medium at the bottom of the well induces, in the last step, an amplification of the absorption measured in dark field configuration. Therefore, a lower LoD has to be expected in that case.
Figure 5:
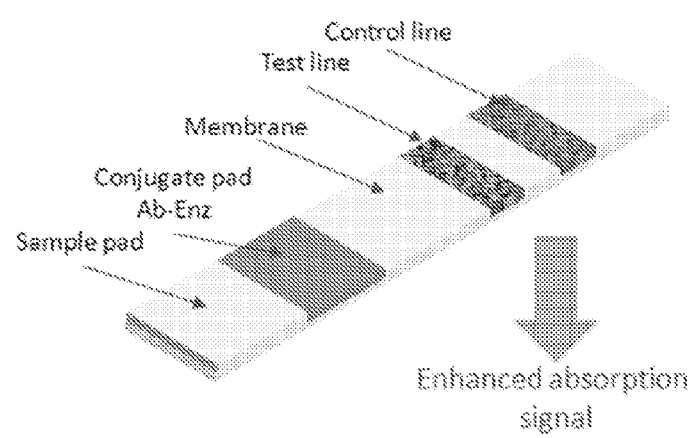
FIG. 5: Implementation of method described to lateral flow dipstick tests where the colour development takes place into a porous highly scattering material that enables enhancement of measured absorption and leading possibly to lower LoD.
Figure 6:
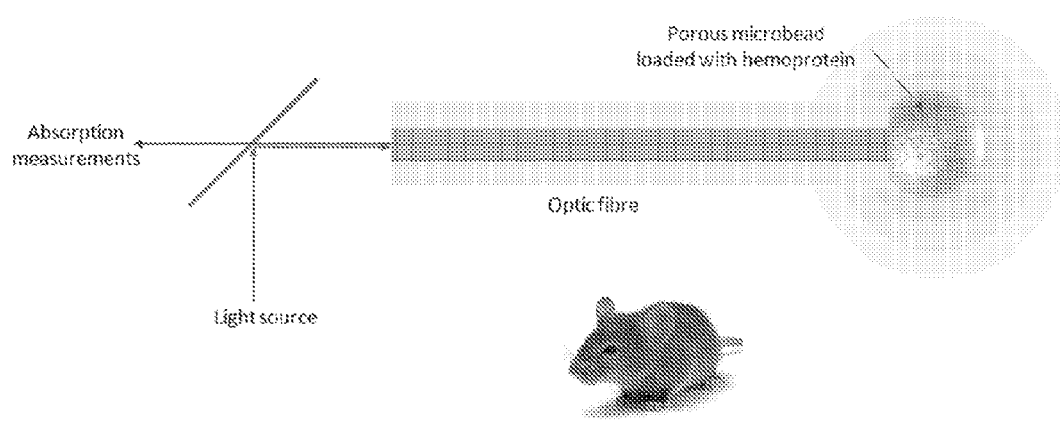
FIG. 6: Sensing probe device for in vitro measurement made of an optic fibre ended with a porous micro bead loaded with hemoprotein.

The detection principle described in this document is implementable to various detection tool configurations such as, for instance but not limited to, ELISA (enzyme-linked immunosorbed assay) (FIG. 4), lateral flow dipstick (FIG. 5) or biosensing microprobe for in vivo measurements (FIG. 6). In all those configurations the common strategy to enhance the signal relies on both the use of a scattering random medium (e.g. porous membrane) in which the colour development takes place and the measurement of absorption in dark field configuration.

The invention claimed is:
1. A method for analyzing an analyte comprising the steps of:
   (a) providing a multiscattering medium that enhances a detection of an electromagnetic cross-section signal of a metalloprotein,
   (b) incorporating the metalloprotein to be analyzed into the multiscattering medium and the analyte is arranged to establish a redox reaction with the metalloprotein,
   (c) contacting the multiscattering medium with electromagnetic radiation,
   (d) obtaining the electromagnetic cross-section spectrum of the metalloprotein, and
   (e) determining from the electromagnetic cross-section spectrum a concentration of the analyte.
2. The method according to claim 1 wherein the electromagnetic cross-section is an absorption cross-section of the metalloprotein.
3. The method according to claim 1 wherein the multiscattering medium is at least one of an aggregate; a suspension; a gel; a porous membrane; a microstructured substrate; and a nanostructured substrate.
4. The method according to claim 1 wherein the analyte is a reaction product of enzymatic or chemical reactions.

5. The method according to claim 1 wherein the step of (c) contacting uses a dark-field electromagnetic radiation illumination.

6. The method according to claim 1 wherein the step of (e) determining further includes:
   determining the concentration of the analyte based on a measurement of a molecular state of the metalloprotein.

7. The method according to claim 6 wherein the molecular state is an oxidation state.

8. The method according to claim 1 wherein the analyte is hydrogen peroxide.

9. The method according to claim 1 wherein the metalloprotein is a cytochrome c.

10. The method according to claim 1, wherein the multiscattering medium enhances an optical cross-section of the metalloprotein.

11. The method according to claim 1, wherein the multiscattering medium provides for an amplification of the electromagnetic cross-section spectrum to suppress a background signal.

* * * * *